United States Patent [19]

Moser et al.

[11] Patent Number: 4,968,785

[45] Date of Patent: Nov. 6, 1990

[54] SUBSTITUTED GLYCOSIDE COMPOSITIONS

[75] Inventors: Kenneth B. Moser; Larson B. Dunn; James C. Schmidt, all of Decatur, Ill.

[73] Assignee: Henkel Kommanditgesellschaft auf Aktien, Duesseldorf, Fed. Rep. of Germany

[21] Appl. No.: 195,250

[22] Filed: May 17, 1988

[51] Int. Cl.$^5$ ............................ C07G 3/00; C07H 1/00
[52] U.S. Cl. ................................. 536/4.1; 536/18.6; 536/124
[58] Field of Search ................... 536/4.1, 18.6, 124

[56] References Cited

U.S. PATENT DOCUMENTS

| | | | |
|---|---|---|---|
| H171 | 12/1986 | McDaniel et al. | 536/4.1 |
| 2,356,565 | 8/1944 | Chwala | 536/17.9 |
| 3,346,558 | 10/1967 | Roth | 536/4.1 |
| 3,475,458 | 10/1969 | McClure et al. | 536/120 |
| 3,737,426 | 6/1973 | Throckmorton | 536/18.3 |
| 3,772,269 | 11/1973 | Lew | 536/4.1 |
| 3,839,318 | 10/1974 | Mansfield | 536/18.6 |
| 3,842,005 | 10/1974 | Moser et al. | 536/50 |
| 3,931,148 | 1/1976 | Langdon | 536/50 |
| 3,974,138 | 8/1976 | Lew | 536/4 |
| 4,232,129 | 9/1980 | Roth et al. | 536/120 |
| 4,349,669 | 9/1982 | Klahr et al. | 536/127 |
| 4,585,858 | 4/1966 | Molotsky | 536/4.1 |
| 4,704,453 | 11/1987 | Lorenz et al. | 536/18.6 |
| 4,713,447 | 12/1987 | Letton | 536/18.6 |
| 4,719,272 | 1/1988 | Tsai et al. | 536/17.4 |
| 4,837,368 | 7/1989 | Lueders et al. | 536/18.6 |

FOREIGN PATENT DOCUMENTS 167488 6/1985 Fed. Rep. of Germany .

OTHER PUBLICATIONS

Starch: Chemistry and Technology, vol. 11, pp. 312–326, 333–350, 403–422 (Academic Press, 1967, R. L. Whistler et al. ed).

J. Thiem et al, "Synthesis and Properties of New Surfactants from Carbohydrates" published in the proceedings of the Second World Surfractants Congress (CESIO).

Chemical Abstracts 53:10046b–10047c, Jun. 10, 1959.

European Patent Reports, Abstract No. 86-009400102, Jan. 1986, (Derwent Publ. Ltd.).

G. W. Hay et al and J. R. Ingle et al. in Methods in Carbohydrate Chemistry, pp. 79–86 (Academic Press, 1964, R. L. Whistler ed.).

W. N. Haworth et al., J. Chem. Soc. 1342 (1931).

M. L. Wolfrom et al., J. Am. Chem. Socl., vol. 63, 1336–1339 (1941).

*Primary Examiner*—Ronald W. Griffin
*Attorney, Agent, or Firm*—Ernest G. Szoke; Wayne C. Jaeschke; Daniel S. Ortiz

[57] ABSTRACT

A method of preparing a composition comprised of a glycoside having a cationic-substituted glycosyl moiety is provided. A cationic starch derivative is reacted with a monohydric alcohol to form cationic-substituted glycosides. Cationic starch derivatives include the tertiary amino, imino, quaternary ammonium or phosphonium, or tertiary sulfonium starch derivatives. Compounds generally characterized as glycosides having cationic-substituted glycosyl moiety are also claimed.

19 Claims, No Drawings

SUBSTITUTED GLYCOSIDE COMPOSITIONS

FIELD OF THE INVENTION

In one aspect, this invention relates to substituted glycoside compositions. In another aspect, this invention relates to methods of making substituted glycoside compositions.

BACKGROUND OF THE INVENTION

Functional groups have been introduced into aldose and ketose saccharide molecules through the formation of acetals or ketals. The reaction of a reducing saccharide at the aldose or ketose moiety with an alcohol results in the formation of an acetal or ketal glycoside composed of two parts: one part is the residue of the saccharide, commonly referred to as the glycosyl moiety, and the other part is the residue of the alcohol, commonly referred to as the aglycone moiety. The glycoside can be useful as a polyol having much greater stability in the presence of alkaline materials than the corresponding reducing saccharide. The use of lipophilic alcohols to form the aglycone moiety of the glycoside can impart surface active properties to the glycoside.

U.S. Pat. Nos. 2,356,565 (Chwala) and 3,931,148 (Langdon) disclose reacting a halo-substituted alcohol with a reducing monosaccharide to form a glycoside having a halo-substituted aglycone moiety and then reacting the resulting glycoside with an organic compound, e.g. a fatty amine, to prepare a glycoside having a substituted aglycone moiety and that has surface-active properties.

U.S. Pat. No. 3,737,426 (Throckmorton) discloses surface-active glycosides prepared by the alcoholysis of starch with a polyol to form a glycoside having an hydroxyl-substituted aglycone and sequentially reacting the resulting glycoside with a short-chain epoxyalkane and a long-chain epoxyalkane.

U.S. Pat. No. 4,719,272 (Tsai et al.) discloses reacting a mono- or low molecular weight polysaccharide with a halohydrin or halo-alcohol to form a halohydrin or glycidyl glycoside and then reacting the resulting glycoside with an unsaturated amine to prepare a monomeric cationic glycoside.

The above methods all link a glycoside substituent to the aglycone moiety of the glycoside molecule rather than the glycosyl moiety by reacting a derivatizing agent with the glycoside. Accordingly, any reaction by-products of the derivatization must be separated from the glycoside itself. Further, the glycoside substituent is labile to cleavage from the molecule upon hydrolysis of the aglycone moiety from the glycoside.

SUMMARY OF THE INVENTION

In one aspect, this invention relates to a method of preparing a composition comprised of a substituted glycoside comprising reacting a cationic starch derivative with a monohydric alcohol to form a composition comprised of a glycoside having a cationic-substituted glycosyl moiety.

Attempts to prepare an alkyl glucoside having cationic substituents at the 2, 3, 4 or 6 positions by reacting an alkyl glucoside with an epoxyalkyl quaternary amine were unsuccessful. However, by reacting a cationic starch derivative with an alcohol, an alkyl glycoside having a cationic substituent was prepared. One advantage of this method resides in the ability to conveniently purify the substituted starch to remove by-products of the derivatizing reaction.

This invention also relates to compounds which have the general formula:

wherein:

G is a glycosyl moiety derived from a reducing saccharide selected from the group consisting of fructose, glucose, mannose, galactose, talose, gulose, allose, altrose, idose, arabinose, xylose, lyxose, ribose or mixtures thereof; R is an aliphatic or aromatic aglycone group containing from 1 to 30 carbon atoms, $R^1$ and $R^2$ are independently alkylene groups having from 2 to 4 carbon atoms each, m is from 0 to about 30, t is from 0 to about 30, x is from 1 to 10, Z is an organic group selected from the group of tertiary aminoalkyl, imino, quaternary ammonium, quaternary phosphonium and tertiary sulfonium, said Z being either directly or indirectly bound to one of the carbons of G or to one of the carbons of $R^2$; y is from 1 to 20; and no more than two Z groups are associated with any one G group. Preferred compounds are those wherein said Z has the formula:

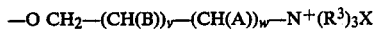

wherein:

A and B are independently hydrogen or hydroxyl; v is from 0 to 18; w is from 0 to 18; each $R^3$ is independently hydrogen or an alkyl group having 1 to 18 carbon carbon atoms which are straight chains or are branched, provided that at least two $R^3$ are alkyl groups and the sum of all carbon atoms in Z is 3 to 50, X is an anion selected from the group consisting of $Cl^-$, $Br^-$, $I^-$, $F^-$, $NO_3^-$ $SO_4^{-2}$, and $PO_4^{-3}$.

As noted above, attempts to prepare an alkyl glycoside within the general formula above by the reaction of an alkyl glycoside with an epoxyalkyl quaternary amine were unsuccessful. However, alcoholysis of a cationic starch allowed the preparation of a compound within the general formula.

DETAILED DESCRIPTION OF THE INVENTION

The method of this invention generally involves the alcoholysis of a cationic starch with a monohydric alcohol to form a cationic glycoside.

Cationic starches are known to those of ordinary skill in the art. The production and uses of cationic starches are described and extensively referenced in *Starch: Chemistry and Technology*, Vol. 11, pp. 403–422 (Academic Press, 1967 R. L. Whistler et al. ed.), the disclosure of which is incorporated herein by reference. Cationic starches typically have a tertiary amino alkyl group (e.g., a dimethylamino-ethyl), an imino group, a quaternary ammonium group (e.g. a trimethylammonium-hydroxypropyl), a quaternary phosphonium group (e.g. tributylphosphonium-methyl) or a tertiary sulfonium group (e.g. a methyl, ethylsulfonium-methyl) bonded to a starch hydroxyl through an organic ether or ester linkage.

Chemically, cationic starch is generally composed of amylose and/or amylopectin molecules having cationic substituents. Amylose is a linear polymer of α-D-glucopyranosyl units linked 1,4 (typically with an average degree of polymerization between about 250 and about 4000 units) and having free hydroxyls at the 2, 3 and 6 positions which can be reacted with a derivatizing agent. Amylopectin is a highly branched polymer of α-D-glucopyranosyl units linked 1,4 with branches at alpha-1,6-linkages spaced an average of from about 12 to about 50 units apart, thus leaving free hydroxyls at the 2 and 3 positions and most (about 95%) 6 positions. The cationic group is generally bonded to the amylose or amylopectin molecule through etherification or esterification of the free hydroxyls of the amylose and amylopectin molecules. The average number of cationic groups per α-D-glucopyranosyl unit is commonly referred as the degree of substitution (D.S.). The D.S. of the cationic starch useful in the method of this invention can vary widely depending upon the desired degree of cationic functionality in the resulting glycoside. In other words, if a cationic glycoside having an average cationic functionality of about n is desired, a cationic starch having a D.S. of n (or greater if some loss of functionality is anticipated, e.g. by transesterification, upon alcoholysis of the cationic starch) should be used. For example, if a glycoside having an average cationic functionality of about 1 is desired, the cationic starch used in the method of this invention should have a D.S. of about 1 (or greater). High D.S. cationic starches are described in detail in U.S. Pat. No. 3,842,005 (Moser et al.) the pertinent disclosure of which is incorporated herein by reference.

Substantially complete alcoholysis of the cationic starch will yield a glycoside that consists substantially of cationic glucoside. Incomplete alcoholysis will result in varying amounts of cationic glycosides of higher saccharides, e.g. cationic maltosides, cationic maltotriosides and the like. Accordingly, the nature and amounts of the particular cationic glycosides present in the product can, to a degree, be adjusted by varying the degree of alcoholysis.

Examples of the cationic reagents that can be reacted with starch to form a cationic starch useful in this invention include a variety of compounds having the desired cationic functionality and the ability to form an ether or ester linkage with the starch by reaction with a free hydroxyl group (or "starchate group" by pre-reaction of the starch with a sufficiently alkaline material). This ability is generally due to the presence in the cationic reagent of a second functionality in addition to the cationic functionality. Because of their stability to subsequent alcoholysis reactions, cationic starch ethers are preferred. Thus, preferred cationic reagents are those able to form an ether linkage with the starch, e.g. beta-haloalkyl; beta, gamma-epoxyalkyl, gamma-halo-beta-hydroxyalkyl; and gamma-haloalkenyl (i.e. beta- and gamma- with respect to the cationic group). The imino cationic starches are generally prepared by reacting a cyano-compound (e.g. a dialkyl cyanamide) with starch under alkaline conditions and then acidifying the imino starch to protonate the imino group. The other cationic groups are generally present in their respective cationic reagent at the time of reaction with the starch, e.g. dialkyamino alkyl groups, (e.g. diethylaminoethyl) trialkylammonium-alkyl (trimethylammonium-2-hydroxylpropyl), trialkylphosphonium-alkyl, and dialkylsulfonium-alkyl.

The alcohols useful in the method of this invention are monohydric alcohols. Preferred alcohols are monohydric alcohols containing from about 1 to about 30 carbon atoms. They may be primary or secondary alcohols, straight or branched chain, saturated or unsaturated (e.g. allyl alcohol, 2-ethylhexenyl alcohol and oleyl alcohol) alkyl or aralkyl alcohols, ether alcohols, cyclic alcohols, or heterocyclic alcohols. Examples of the monohydric alcohols which may be employed in the present invention include methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, heptadecyl alcohol, octadecyl alcohol, eicosyl alcohol, pentacosyl alcohol, oleyl alcohol, isoberneol alcohol, hydroabietyl alcohol, phenoxyethanol, phenoxypolyethoxyethanol containing five ethoxy groups and 2-methyl-7-ethyl-4-undecanol.

A preferred group of alcohols are alkanols having the formula ROH wherein R presents an alkyl group having from 1 to 4 carbon atoms. Another group of alcohols are those wherein R represents an alkyl radical having from 8 to 20, preferably 12 to 18, carbon atoms.

The alcoholysis of the cationic starch is a transglycosidation reaction, i.e. starch is reacted with a monohydric alcohol (and optionally water which may hydrolyze the starch in situ for conversion to the glycoside by glycosidation thereof with alcohol), typically in the presence of an acid catalyst (e.g. mineral acids such as hydrochloric, sulfuric, or nitric) which serves to ensure a practical rate of reaction between the cationic starch and monohydric alcohol. The transglycosidation can be direct (i.e. an alcohol having the structure desired as the aglycone moiety is used to alcoholyze the starch) or stepwise (i.e. an intermediate alcohol, e.g. butanol, is first reacted with the starch to form an intermediate glycoside which is then reacted with the alcohol that will yield the desired aglycone). The transglycosidation may be continuous as disclosed in U.S. Pat. No. 4,223,129 (Roth et al.) Longer chain monohydric alcohols, e.g. alkanols having more than four carbon atoms, may be insufficiently compatible with the cationic starch to react with the starch (or intermediate cationic butyl glycoside) at a practical rate of reaction in aqueous media, particularly if the cationic group is comprised of only short chain organic groups. In such a case, highly miscible organic solvents such as dimethyl sulfoxide, dimethylformamide, etc., and/or surface active agents, e.g. alkyl oligosaccharides, and/or using as a catalyst the acid form of a long chain alkylsulfonic or alkylbenzene sulfonic acid such as those disclosed in U.S. Pat. No. 4,713,447 (Lexton) (e.g. dodecylbenzenesulfonic acid) may be useful in the reaction mixture to achieve practical rates of reaction between the cationic starch and higher alkanol.

The compounds of this invention having the general formula outlined above can be referred to as a glycoside having a cationic-substituted glycosyl moiety in that they are glycosides having cationic groups bonded to the glycosyl moiety of the glycoside rather than the aglycone moiety of the glycoside. These cationic glycosides can be derived from monosaccharides or polysaccharides hydrolyzable or alcoholyzable to monosaccharides. In the case of the preferred cationic glycosides, i.e. cationic glycosides derived from starch which are comprised predominantly of cationic glucosides, many attempts to introduce cationic functionality into the glycoside failed and, thus, the method of this invention (i.e. the alcoholysis of a cationic starch) should be used to prepare a cationic glycoside of this invention. The other cationic glycosides should be susceptible to synthesis from cationic monosaccharides or cationic polysaccharides. For example, the cationic polyfructose inulin may be reacted with a cationic reagent and then subjected to alcoholysis to prepare a fructoside having a cationic-substituted fructosyl moiety.

The following examples will further illustrate the invention and comparative inquiries made in connection with investigations related to this invention. All parts, ratios and percentages expressed both above and in the following are by weight (with the notable exception of D.S.) unless otherwise indicated in context.

EXAMPLES

Two types of mixtures of cationic glycosides, methyl and butyl, were synthesized by the alcoholysis of cationic starch having a D.S. of 1.0.

EXPERIMENTAL

A. Attempts at Synthesis

1. Procedure for Synthesizing Cationic Glycosides from Alkyl Glycosides

Cationic epoxide was generated in situ by adding 1.0 eq sodium hydroxide (0.0155 moles, 0.62 g) to 1.0 equiv. QUAB 188 (0.0155 moles, 4.38 g of a 66.37% aq. solution, 2.91 g solids) of 0° C. and reacting for 30 min. Water was removed by azeotrope by adding 25 ml isopropyl alcohol and evaporating to dryness, followed by the addition of 100 ml isopropyl alcohol and 1.0 equiv. alpha methyl glucoside (0.0155 moles, 3.0 g), with 0.2 equiv. sodium hydroxide (0.0031 moles, 0.124 g) added as a catalyst. The reaction mixture was heated to 70° C. for 2 hours, followed by evaporation of the solvent under reduced pressure. A sample of the residue was dissolved in deuterated water (D$_2$O) and examined by $^{13}$C NMR; the alpha-methyl glucoside was unchanged. The above example in Run A in Table 1, below. Similar procedures were used for Runs B-L with the exceptions noted in Table 1.

2. Procedure for Synthesizing Cationic Allylic Alcohol

A mixture of 100 g (1.69 moles) trimethylamine and 130.4 g (1.41 moles) epichlorohydrin was stirred at room temperature in 700 ml acetone for 28 hrs. The crystals that formed were collected, washed with diethyl ether until nearly colorless and weighed to give 199.05 g (93.1%) of an off-white solid, m.p. 158°–160° C. (lit. 164°–165° C., ref. 5), identified as N-(3-hydroxy-1-propenyl) trimethylammonium chloride (spectral data is in Appendix). When the reaction was repeated using an excess of epichlorohydrin, the same product was produced, albeit in lower yield (74.3%) and purity (m.p. 152°–154° C.).

B. Procedure for Alcoholysis of Cationic Starch

A sample of a cationic starch (prepared by reacting 2-epoxypropyl trimethyl ammonium chloride with pearl corn starch to a D.S. of 1.0) in water at 50% dry solids was twice treated with an anionic/cationic mixed bed resin (available from Rohm & Haas, Co. as Amberlite TM MB-1) to remove salt impurities, filtered and dried to a sticky solid. The dried cationic starch was slurried with the 250 mL of appropriate alcohol (methanol or butanol)/100 g starch, 0.1% p-toluenesulfonic acid (based on starch) was added, and the entire mixture was added to a stainless steel Parr bomb and heated to about 140° C. for 1 hr. The sticky white suspension was evaporated, analyzed by carbon-13 NMR and found to be a mixture of cationic α- and β-glucopyranosides, furanosides and other minor products such as higher degrees of polymerization, levoglucosan and levulinates.

C. Use of Alternate Catalysts

1. Preparation of Cationic Butyl Glucoside

To a 500 ml flask equipped with a mechanical stirrer, thermometer, and Dean-Stark Trap was added 300 g butanol, 25 g hexane, and 0.5 g of commercially available linear dodecylbenzenesulfonic acid. The mixture was heated to reflux and 50 g of ion exchanged cationic starch (as described above in B but only treated once and without drying) was added dropwise (as a 44% solution in water) over a 30 minute period. After about 4 hours, distillation of water had slowed markedly and the resulting reaction mixture was cooled. The butanol was decanted and the remaining solid residue was washed with two portions of hexane. The solid was then dissolved in 200 ml methanol and the pH was adjusted to 7.5. A small amount of insoluble material was filtered off and the methanol was evaporated on a rotary evaporator to provide a butanol-insoluble fraction was adjusted to pH 6 and the butanol was evaporated. The resulting fractions were analyzed by carbon NMR. The reaction product of both fractions was found to be a mixture containing cationic glycosides, including butylated components. The butanol-soluble fraction also appeared to contain a salt form of the cationic species and the catalyst.

2. Preparation of Cationic Octyl Glucoside

To a 500 ml flask equipped with a mechanical stirrer, thermometer, addition funnel, distillation head, and aspirator vacuum is added 200 g octanol, 0.4 g of commercially available linear dodecylbenzenesulfonic acid, and 10 g of alkyl polyglycoside as a compatibilizing agent. The mixture is heated to 95°–105° C. and 40 g of cationic butyl glucoside as from the previous example in 100 ml methanol is added dropwise with stirring. When addition is complete, vacuum is applied and heating is continued for one hour. Sufficient base is added to neutralize the acid catalyst. The temperature and vacuum are increased as required to distill off 100–150 g of the octanol. The mixture is cooled and 150 ml of water is added. Residual octanol is extracted by washing with three portions of hexane.

DISCUSSION

A. 1. Methyl Glucoside Fails to React with Cationic Epoxide

Early attempts to synthesize a cationic methyl glucoside involved the use of QUAB 188 (66.37% in water) a cationic chlorohydrin from Degussa, in which the epoxide is generated in-situ by the reaction of the chlorohydrin with aqueous sodium hdyroxide. Excess sodium hydroxide (pH=11) was then added to catalyze the reaction of methyl glucoside with the epoxide. The only reaction that occurred was either hydrolysis of the epoxide to a diol or ring-opening of the epoxide to an allylic alcohol, both products being identified by carbon-13 NMR. In many cases, when milder conditions were used (lower pH, lower temperature, shorter reaction time), starting materials were recovered unchanged. Table I lists the variety of conditions used in the attempts to react methyl glucoside with the cationic epoxide.

TABLE I

ATTEMPTED REACTIONS OF METHYL GLUCOSIDE WITH CATIONIC EPOXIDE

| Run | Solvent | pH | Temp. (°C.) | Reaction Time (hrs.) | Results (a) |
|-----|---------|-----|-------------|----------------------|-------------|
| A | Water | 11 | 70 | 2 | (i) |
| B | Water | 9 | 70 | 2 | N.R. |
| C | Water | 11 | 0–70 | 2 | N.R. |
| D | Water | 8–9 | 0–70 | 2 | N.R. |
| E | Water | (b) | 70 | 2 | (j) |
| F | IPA/Water(c) | — | 0–r.t. | 2 | N.R. |
| G | IPA/Water(d) | — | 0–70 | 2 | N.R. |
| H | IPA/Water(d) | — | 0–r.t. | 1 | N.R. |
| I | Acetonitrile | (e) | 0–r.t. | 1 | N.R. |
| J | IPA | (f) | 0–70 | 2 | N.R. |
| K | IPA | (g) | 70 | 1 | N.R. |
| L | IPA | (h) | 70 | 1 | N.R. |

(a) - Based on carbon-13 analysis of reaction mixture
(b) - 1.05 eq. NaOH-total base used
(c) - 80/20 by volume
(d) - 90/10 by volume
(e) - Sodium salt of methyl glucoside
(f) - 1.2 eq. NaOH-total base used
(g) - Sodium methoxide catalyst, crystalline epoxide (runs A–J all used epoxide generated from QUAB 188)
(h) - Sodium salt of methyl glucoside, crystalline epoxide
(i) - Analyzed product as diol and methyl glucoside
(j) - Analyzed product as diol, allylic alcohol, epoxide and methyl glucoside After the initial failures, it was thought that water might be interfering with or slowing the reaction. Therefore, some reactions of QUAB 188 with methyl glucoside were tried in mixtures of isopropyl alcohol (IPA) and water. However, no reaction was observed in the mixed solvent systems tried, or when anhydrous conditions (acetonitrile or IPA alone) were tried (see Table I).

Lastly, methyl glucoside and its isolated sodium salt were reacted with crystalline cationic epoxide in IPA, again with no observable reaction (see Table I).

A. 2. Synthesis of Crystalline Cationic Epoxide

When it was thought that the presence of water in the reaction mixtures of methyl glucoside and cationic epoxide was undesirable, crystalline cationic epoxide was synthesized according to U.S. Pat. No. 3,475,458 (McClure et al.), so the epoxide no longer had to be generated in-situ. However, initial attempts to synthesize the epoxide by the McClure et al. procedure using acetone as the solvent produced a different product, a cationic allylic alcohol, readily identified by its NMR spectra and its melting point. Apparently, the McClure et al. procedure does not work in polar organic solvents as the product does not precipitate fast enough to prevent ring-opening catalyzed by trimethylamine. The McClure et al. procedure was reproduced to give the desired product when a non-polar solvent system, such as chloroform/hexane, was used.

The cationic allylic alcohol may be of use as an alternate cationizing reagent, although attempts to use it in a transglucosidation reaction with methyl glucoside were fruitless (no methanol driven off).

B. Alcoholysis of Cationic Starch Successfully Produces Mixture of Cationic Glycosides Since conditions could not be found to react methyl glucoside with cationic epoxide, it was decided to try reversing the steps of the overall synthesis, remembering that methyl glucoside is produced by the methanolysis of starch. Therefore, a 1.0 D.S. cationic starch was treated with methanol and acid producing a mixture of methyl cationic glycosides, as identified by carbon-13 NMR.

A subsequent reaction was done using butanol to produce a mixture of butyl cationic glycosides.

C. Cationic Butyl Glucoside

Further work with alcoholysis of a cationic starch using as a catalyst the acid form of an anionic surfactant indicated that such catalysts are useful in the alcoholysis of a cationic starch (as well as their expected utility in the transglycosidation of a butyl cationic glycoside to an octyl cationic glycoside).

What is claimed is:

1. A process for the preparation of substituted glycosides which comprises reacting a cationic starch derivative with monohydric alcohol to form glycosides having a cationic substituted glycosyl moiety.

2. A process of claim 1 further comprising purifying said cationic starch derivative before reacting said starch derivative with an alcohol.

3. A process of claim 2 further comprising reacting a starch with a derivatizing agent to form said cationic starch derivative prior to said purifying.

4. A process of claim 1 wherein said starch derivative is selected from the group consisting of etherified starches and esterified starches.

5. A process of claim 1 wherein said starch derivative has a degree of substitution of at least about 0.7.

6. A process of claim 1 wherein said monohydric alcohol is an alkanol having from 1 to about 30 carbon atoms.

7. A process of claim 6 wherein said monohydric alcohol is an alkanol having from 1 to about 4 carbon atoms.

8. A process of claim 6 wherein said monohydric alcohol is an alkanol having from 5 to about 30 carbon atoms.

9. A process of claim 8 wherein said cationic starch derivative and said monohydric alcohol are reacted in the presence of a long chain alkylsulfonic acid or alkylbenzene sulfonic acid.

10. A process of claim 1 whrein said cationic starch derivative and said monohydric alcohol are reacted in the presence of a long chain alkylsulfonic acid or alkybenzene sulfonic acid.

11. A process of claim 1 wherein said cationic starch derivative is comprised of a member selected from the group consisting of a tertiary amino alkyl group, an imino group, a quaternary ammonium group, a quaternary phosphonium group, and a tertiary sulfonium group.

12. A process of claim 11 wherein said selected group is comprised of at least one alkyl group having more than four carbon atoms.

13. A process of claim 12 wherein said monohydric alcohol is an alkanol having from 5 to about 30 carbon atoms.

14. Compounds which have the formula:

wherein:

G is a glycosyl moiety derived from a reducing saccharide selected from the group consisting of fructose, glucose, mannose, galactose, talose, gulose, allose, altrose, idose, arabinose, xylose, lyxose, ribose or mixtures thereof; R is an aliphatic or aromatic aglycone group containing from 1 to 30 carbon atoms, $R^1$ and $R^2$ are independently alkylene groups having from 2 to 4 carbon atoms each, m is from 0 to about 30, t is from 0 to about 30, x is from 1 to 10, Z is an organic group selected from the group consisting of tertiary aminoalkyl, imino, quaternary ammonium, quaternary phosphonium and tertiary sulfonium, said Z being either directly or indirectly bound to one of the carbons of G or to one of the carbons of $R^2$; y is from 1 to 20; and no more than two Z groups are associated with any one G group.

15. A compound of claim 14 wherein said Z has the formula:

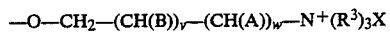
—O—$CH_2$—$(CH(B))_v$—$(CH(A))_w$—$N^+(R^3)_3$X wherein:

A and B are independently hydrogen or hydroxyl; v is from 0 to 18; w is from 0 to 18; each $R^3$ is independently hydrogen or an alkyl group having 1 to 18 carbon carbon atoms which are straight chains or are branched, provided that at least two $R^3$ are alkyl groups and the sum of all carbon atoms in Z is 3 to 50, X is an anion.

16. A compound of claim 15 wherein x is an anion resulting from the neutralization of an organic or inorganic acid.

17. A compound of claim 15 wherein x is selected from the group consisting of $Cl^-$, $Br^-$, $I^-$, $F^-$, $NO_3^-$, $SO_4^{-2}$, $PO_4^-$, alkylsulfonate, and alkylbenzenesulfonate.

18. A compound of claim 14 wherein G is selected such that G is the residue of a cationic starch derivative.

19. A compound of claim 14 wherein G is glucose, R is an alkyl having from 1 to 30 carbon atoms, m is 0, x is 1, t is 0, and Z is —$CH_2$—CH(B)—CH(A)—$N^+(CH_3)_3$X wherein one of A and B is hydrogen and the other is hydroxyl and X is selected from $Cl^-$ and $Br^-$.

* * * * *